(12) United States Patent
Higaki et al.

(10) Patent No.: US 8,607,629 B2
(45) Date of Patent: Dec. 17, 2013

(54) METHOD FOR ASSESSMENT OF FORCE PROPERTIES GENERATED BY THE FIBER TIP

(75) Inventors: Masato Higaki, Kobe (JP); Naohiro Morita, Nishinomiya (JP); Yoko Osada, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 446 days.

(21) Appl. No.: 12/958,719

(22) Filed: Dec. 2, 2010

(65) Prior Publication Data

US 2011/0137828 A1 Jun. 9, 2011

Related U.S. Application Data

(60) Provisional application No. 61/266,186, filed on Dec. 3, 2009.

(51) Int. Cl.
*G01L 5/04* (2006.01)

(52) U.S. Cl.
USPC .............................................. 73/160; 73/159

(58) Field of Classification Search
USPC .................................................. 73/159, 160
See application file for complete search history.

(56) References Cited

U.S. PATENT DOCUMENTS

| | | | | |
|---|---|---|---|---|
| 2,627,179 A | * | 2/1953 | Grant | 73/160 |
| 3,921,443 A | * | 11/1975 | Yates | 73/817 |
| 4,061,022 A | * | 12/1977 | Yates | 73/764 |
| 4,583,562 A | * | 4/1986 | Stewart | 132/212 |
| 5,461,925 A | * | 10/1995 | Nguyen et al. | 73/789 |
| 6,817,222 B2 | | 9/2003 | Tachi | |
| 2003/0178556 A1 | | 9/2003 | Tachi | |
| 2007/0040107 A1 | | 2/2007 | Mizota et al. | |
| 2007/0043508 A1 | | 2/2007 | Mizota et al. | |
| 2008/0096293 A1 | | 4/2008 | Suhir | |
| 2008/0245955 A1 | | 10/2008 | Tachi | |

(Continued)

FOREIGN PATENT DOCUMENTS

| | | |
|---|---|---|
| GB | 2081457 | 2/1982 |
| JP | 2007-147443 A | 6/2007 |

OTHER PUBLICATIONS

"Lateral Mechanical Coupling of Stereocilia in Cochlear Hair Bundles"; Mattias G. Langer, et al; Biophysical Journal vol. 80, Jun. 2001, 2608-2621.

(Continued)

*Primary Examiner* — Max Noori
(74) *Attorney, Agent, or Firm* — Linda M. Sivik

(57) ABSTRACT

A method for assessment of force properties generated by the fiber tip of one or more fibers, comprising the steps of: (a) providing a fiber sample of one or more fibers, the fiber sample having a free portion and an end; (b) suspending the fiber sample over a tactile sensor at least 0.1 mm away in the vertical direction from the tactile sensor; wherein the fiber sample or the tactile sensor is connected to a means for vertically moving either the fiber sample or the tactile sensor toward each other; (c) surrounding the free portion of the fiber sample with a cover which surrounds the free portion over some length of the free portion and stably positioned; wherein the cover guides the direction of the free portion in a more or less vertical orientation through the steps hereof; (d) vertically moving the fiber sample or the tactile sensor such that the end of the fiber sample contacts the tactile sensor; (e) providing the tactile sensor with means for measuring the distribution of force vectors generated by the contact of the end of the fiber sample; and (f) assessing the force properties based on the distribution of force vectors.

15 Claims, 1 Drawing Sheet

(56) References Cited

U.S. PATENT DOCUMENTS

2010/0106679 A1* 4/2010 Yamaguchi et al. .......... 706/54
2010/0277475 A1* 11/2010 McAdams et al. .......... 345/420

OTHER PUBLICATIONS

Kamiyama, Kajimoto, Inami, Kawakami, Tachi, "Development of A Vision-based Tactile Sensor", Trans. of IEEJ Sensors and Micromachines society, pp. 16-22, vol. 123, No. 1, Jan. 2003.

"Quantification and Prevention of Hair Damage"; Tate, M.I. et al., J. Soc. Cosmet Chem., 44, 347-374 (Nov./Dec. 1993).

K Kamiyama, Kajimoto, Kawakami, Tachi, "Evaluation of a Vision-based Tactile Sensor", Proc. of 2004 International Conference on Robotics and Automation, WP-6, Apr. 2004.

International Search Report; PCT/US2010/057768, Mailing Date Mar. 16, 2011; 11 pages.

* cited by examiner

METHOD FOR ASSESSMENT OF FORCE PROPERTIES GENERATED BY THE FIBER TIP

CROSS REFERENCE TO RELATED APPLICATIONS

This application claims the benefit of U.S. Provisional Application No. 61/266,186 filed on Dec. 3, 2009.

FIELD OF THE INVENTION

The present invention relates to a method for assessment of force properties generated by the fiber tip. The present invention is also useful for assessing the decreasing of the stimulus generated by the fiber tip, and softness of fibers. The present invention is particularly useful for demonstrating the benefit of a composition for decreasing the stimulus generated by the fiber tip and softness of fibers. The present invention may be utilized for supporting advertising claims.

BACKGROUND OF THE INVENTION

The fiber tip of fibers such as mammalian hair provides a certain stimulus when they touch the surface of the skin, for example by the palm of a hand when treating the fibers, or by neck, shoulder, or chest area, merely based on gravity. Relatively strong stimulus of the fiber tip may be described as stiffness, prickly feel or itchy feel, and is considered a negative sensory feel by some consumers. The force generated by the fiber tip, which is perceived as stimulus, varies depending on the properties of the fiber including, but not limited to, factors such as the roughness of the fiber tip, and the flexibility over the length of the fiber. Usually, the smoother the fiber tip, and the softer the fiber is along its entire length, the lower the force generated upon the fiber tip touching the skin. When the fiber is mammalian hair, stronger fiber tip force or stimulus may be recognized by some consumers as "lack of softness of the hair", and associated with poor conditions of the hair, such as split ends, dryness, roughness of cuticle, and overall stiffness, brittleness, or inflexibility of the hair. Hair conditioning or hair treatment compositions designed for imparting softness to the hair may alleviate the stimulus generated by the fiber tip by, not only imparting softness to the hair, but also improving such poor conditions. Hence, the unpleasant stimulus, such as stiffness or prickly feel generated by the hair fiber tip, may be considered as a sign of less treated or conditioned hair by consumers who prefer soft hair.

Some consumers have the habit of measuring the softness of the hair by holding a strand of hair from beneath, to sense the prickly feel on the palm. When the prickly feel of pre-conditioned hair fiber tip is reduced after conditioning, consumers who prefer soft hair may assess that the hair has been well conditioned. Such method, however, is subjective and is different depending on the consumer. Methods for objectively measuring the condition of the hair have been proposed, for example by microscopy, or by detecting properties of the surface of the skin such as in U.S. Pat. No. 6,817,222. However, these methods usually require many types of equipment and provide data to be interpreted by the skilled person, while being barely understandable for the general consumer. There remains a need for a method allowing a direct visualization resembling and correlating with the "stimulus sensing" provided by the general consumer.

Based on the foregoing, there is a need for a method allowing a direct visualization of the force generated by the hair fiber tip and thereby allowing a direct visualization of the benefit of a hair care composition for decreasing stimulus generated by the hair fiber tip. In addition, there is a need for a method which can be easily understood by the non-skilled person, including the general consumer and/or the salon stylist. There is also a need for a method for supporting advertising claims about the benefit of a hair care composition for decreasing the stimulus generated by the hair fiber tip. There is also a need for a method for supporting advertising claims about the comparison of the benefit of at least two hair care compositions for decreasing the stimulus generated by the hair fiber tip, and therefore, for making the hair soft. Finally, there is a need for a method of marketing a hair care composition, which composition is capable of decreasing the stimulus generated by the hair fiber tip, and therefore is capable of making the hair soft.

SUMMARY OF THE INVENTION

In a first aspect, the present invention relates to a method for assessment of force properties generated by the fiber tip of one or more fibers, comprising the steps of:
  (a) providing a fiber sample of one or more fibers, the fiber sample having a free portion and an end;
  (b) suspending the fiber sample over a tactile sensor at least 0.1 mm away in the vertical direction from the tactile sensor; wherein the fiber sample or the tactile sensor is connected to a means for vertically moving either the fiber sample or the tactile sensor toward each other;
  (c) surrounding the free portion of the fiber sample with a cover which surrounds the free portion over some length of the free portion and stably positioned; wherein the cover guides the direction of the free portion in a more or less vertical orientation through the steps hereof;
  (d) vertically moving the fiber sample or the tactile sensor such that the end of the fiber sample contacts the tactile sensor;
  (e) providing the tactile sensor with means for measuring the distribution of force vectors generated by the contact of the end of the fiber sample; and
  (f) assessing the force properties based on the distribution of force vectors.

In another aspect, the present invention relates to a method for demonstrating the benefit of a hair conditioning composition, which composition is capable of decreasing the stimulus generated by the hair fiber tip, the method comprising the steps of:
  (1) providing one or more fibers to make a first fiber sample and another one or more fibers to make a second fiber sample;
  (2) treating the first fiber sample with a first hair conditioning composition and optionally treating the second fiber sample with a second hair conditioning composition;
  (3) independently assessing the force properties of the fiber tip of the first and second fiber samples according to the method mentioned above; and
  (4) comparing the assessed force properties of the first and second fiber samples.

In yet another aspect, the present invention relates to a method for marketing a hair conditioning composition by demonstrating the benefit of a hair conditioning composition, which composition is capable of decreasing the stimulus generated by the hair fiber tip or providing the hair soft, the method comprising the steps of:
  (1) offering for sale the hair conditioning composition,
  (2) advertising the benefit of the hair conditioning composition as decreasing the stimulus generated by the hair fiber tip or providing the hair soft; and
  (3) providing the demonstration mentioned above.

BRIEF DESCRIPTION OF THE DRAWINGS

While the specification concludes with claims particularly pointing out and distinctly claiming the invention, it is believed that the present invention will be better understood from the following description of preferred, nonlimiting embodiments and representations taken in conjunction with the accompanying drawings in which:

DETAILED DESCRIPTION OF THE INVENTION

Figure 1:
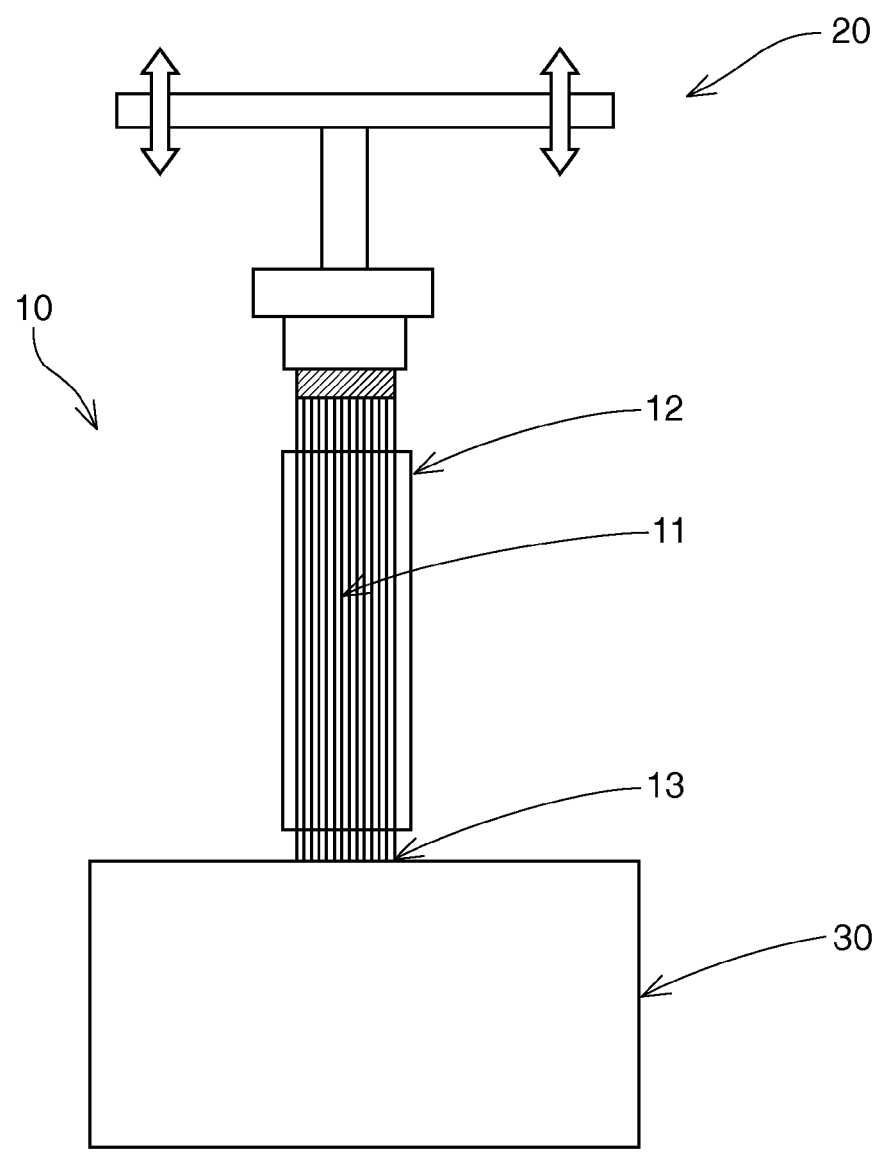
FIG. 1 is a preferred embodiment of a measuring equipment for the present method.

The present invention relates to a method for assessment of force properties of the fiber tip of a sample of one or more fibers, by vertically moving and contacting the sample against a tactile sensor. The invention may be useful to assess the stimulus generated by the fiber tip of the fiber, or the softness of fiber. The invention may also be useful to demonstrate the benefit of a composition, such as a hair care composition, for decreasing the stimulus generated by the fiber tip of the fiber, or providing softness to the fiber. The invention may also be useful to compare the benefit of at least two compositions for decreasing the stimulus generated by the fiber tip of the fiber, or providing the fiber soft. The invention may also be useful for marketing a composition, such as a hair conditioning composition.

The inventors have found that force properties generated by contact of the fiber tips, e.g. mammalian hair, can be assessed by a method comprising suspending a fiber sample over a tactile sensor, and vertically moving the fiber sample or the tactile sensor toward each other so that the end of the fiber sample contacts the tactile sensor, the tactile sensor having means for measuring the distribution of force vectors generated by such contact. Upon vertically moving either the fiber sample or the tactile sensor, the sample is surrounded with a cover which is stably positioned, which surrounds the free portion of the fiber sample over some of the length of the free portion, and guides the direction of the free portion in a more or less vertical orientation. Absent the cover, the free portion may be easily bent or may slip away in the horizontal direction upon contact of the tactile sensor, and interfere with accurate assessment of the force properties. The cover prevents such slipping of the free portion, or bending of the free portion. Depending on the length of the free portion and how the fiber sample or tactile sensor is moved, the cover may surround the free portion over its entire length, or limited length. Specifically, the inventors have found that the force properties thus generated by contact of the fiber tip more or less correlates with the stimulus that the consumer experiences, for example when holding a strand of hair from beneath to sense the prickly feel on the palm. The greater the magnitude of the force, the greater the stimulus is expected to be felt by the consumer. Without being bound by theory, it is believed that the force properties generated by contact of the fiber tip relate to the softness of the fiber, such as hair. Some consumers who prefer soft hair associate softness of the hair with degree of conditioning of the hair. Thus, for such consumers, the less the magnitude of the force, the less the stimulus generated by the hair fiber tip, and the better perceived the condition of the hair.

The inventors have also found that this method may be useful for supporting advertising claims. When the sample is treated with a composition, the method is useful for demonstrating the benefit of the composition for decreasing the force properties of the fiber tips upon contact. This demonstration is useful for supporting advertising claims about the benefit of this composition for decreasing the stimulus generated by the fiber tip of the fiber. Particularly, the inventors have found that this method allows the non-skilled person, i.e. the general consumer or hair stylist, to easily assess the benefit of a composition and to easily compare this benefit with the benefit of other compositions and/or with the absence of treatment, when displayed in an appropriate manner. Without being bound by theory, it is believed that the non-skilled person wishes the advertising claims to be proved or supported by experimental results. It is also believed that conducting this method in front of the consumer, as a live experiment or via a recorded film, may convince him/her of the benefit of the composition and may convince him/her to buy and/or to use the composition.

The present method is useful for demonstrating the benefit of a composition by comparing the force properties of the fiber tip of a fiber sample before and after treatment with the composition. Without being bound by theory, it is believed that when the sample is treated with a composition having the ability to decrease the stimulus generated by the hair fiber tip, or provide the hair soft, the force properties generated by the fiber tip of the fiber sample is decreased.

The present method is also useful for comparing the benefit of at least 2 compositions by comparing the force properties of the fiber tip of a fiber sample treated with a first composition and a second composition. Without being bound by theory, it is believed that when the sample is treated with a composition having better ability to decrease the stimulus generated by the hair fiber tip, the less force properties are generated by the hair fiber tip of the fiber sample.

The method comprises the step of providing at least one sample of one or more fibers having a free portion and an end. As used herein, "fiber" means any fiber that is susceptible to generate a tactile sensation of its fiber tip. Particularly benefiting of the present method is mammalian hair, more preferably human, horse, cat, dog hair, still more preferably human hair. Alternatively, the fiber may be any natural fiber or synthetic fiber used for various applications, including fabrics, textile, garment, nonwovens, paper, etc. By "fiber tip" is meant the cross section of the fiber end and its vicinity of one piece of fiber or a strand of fiber.

The fiber sample may be a multitude of hair which are stranded together at one end, and commonly called hair switches by one skilled in the art. Such fiber sample is suspended vertically with the free portion of said fibers hanging down such that the fiber ends are all in substantially the same horizontal plane. The fiber sample is preferably a strand of mammalian hair having a weight of from 0.1 g to 200 g, more preferably from 2 g to 50 g. The fiber sample preferably has a length of from 1 cm to 150 cm, more preferably from 1 cm to 50 cm, still more preferably from 5 cm to 30 cm. When at least two fiber samples are provided for comparison, these samples have the same number of individual hair with a deviation of +/−50%, preferably +/−30%, more preferably +/−10%, hair between samples.

The present method is explained according to a preferred embodiment of measuring equipment thereof, referring to FIG. 1. The fiber sample 10 is suspended and connected to a means for vertically moving the fiber sample 20 wherein the fiber sample has a free portion 11 and an end 13. Preferably, the end of the free portion is accurately evenly trimmed so that the fibers are all in substantially the same horizontal plane. The means for vertically moving the fiber sample 20 is preferably one that is capable of moving the sample in a fixed speed for an accurate distance. The end 13 of the fiber sample is the portion which contacts the tactile sensor for measuring the force properties of the fiber tip of the fiber sample. The free portion of the fiber sample is surrounded with a cover 12 which surrounds the free portion over some length of the free portion and stably positioned at least 0.1 mm away in the vertical direction from a tactile sensor 30; wherein the cover 12 guides the direction of the fiber sample in a more or less vertical orientation through the steps hereof. The cover 12 is stably positioned, while only the fiber sample moves vertically. The distance between the lower end of the cover and the tactile sensor is so adjusted such that the fiber effectively contacts the tactile sensor 30, namely, the end 13 does not slip away, and the free portion is not easily bent. The cover 12 may be cylindrical, cuboid or otherwise in shape, so long as the void has a slightly greater diameter or greater width than the width of the fiber sample. The cover can be made of any rigid material which is not deformed during the measurement by contact of the fiber, and is preferably transparent or translucent for visibility. The distance between the lower end of the cover and the tactile sensor, and the shape and dimension of the cover 12 are so adjusted to make end of the fiber sample effectively contact the tactile sensor, taking into consideration the rigidity of the fiber, diameter of each piece of fiber, dimensions of the fiber sample, length of the fiber sample, and other characteristics. Preferably, the distance between the lower end of the cover 12 and the tactile sensor 30 is from about 0.1 mm to about 15 mm. Preferably, the fiber sample and the cover are initially positioned such that the lower end of the fiber sample and cover are matched to be in substantially the same horizontal plane.

The fiber sample thus positioned is vertically moved downward, such that a certain length of the free portion from the end moves outside the cover, and contacts the tactile sensor 30. The tactile sensor 30 is provided with means for measuring the distribution of force vectors generated by the contact of the end. Finally, the force properties based on the distribution of force vectors are assessed. The assessment is described at least as the magnitude of the force, preferably by all three of distribution, magnitude, and direction of the force.

In one highly preferred embodiment, the tactile sensor comprises a transparent elastic body, a set of markers distributed inside the elastic body, and a color CCD camera for acquiring the movements of the markers, wherein the movement is generated by contact of the end 13 to the surface of the elastic body, whereby the elastic body is deformed by the contact and thereby providing variation information of the markers. The elastic body has a horizontal plane in the x-y direction and a depth in the z-direction. The markers may be provided in a set distributed along the x-y direction. The interval and distribution of the markers may be adjusted for collecting the desired amount of information in the desired precision and reproducibility. The set of markers may also be provided in 2 different depths in the z direction. The CCD camera is preferably positioned away from the elastic body in the z direction for capturing the movement of the markers from underneath the elastic body. The 2 set of markers may be provided in different colors, such as red and blue, for easy resolution by the CCD camera. The surface of the elastic body, except for the plane facing the CCD camera, is preferably colored black to shield any optical movement unrelated to the measurement. Highly preferred herein are optical tactile sensors described in US Patent Publications 2008/0245955A, 2007/0040107A, 2007/0043508A, 2003/0178556A, and Japanese Patent Publications 2007-147443A and commercially available under the tradename GelForce available from Nitta Corporation (Osaka, Japan).

When the tactile sensor is an elastic body, such as that described above, the vertical moving of the fiber sample may continue beyond the first point of contact of the end of the fiber sample with the surface of the tactile sensor. Namely, the fiber sample may be pressed against the elastic body. In this instance, the cover should be made of rigid material which is capable of pressing into the elastic body. By assessing the force properties of the end of the fiber beyond the first point of contact, the behavior of the fiber sample after first point of contact, such as flexibility of the fiber sample, may be measured. Further, such measurement beyond first point of contact better resembles the consumer's habit of measuring the softness of hair by holding a strand of hair from beneath, to sense the prickly feel on the palm.

Figure 2:
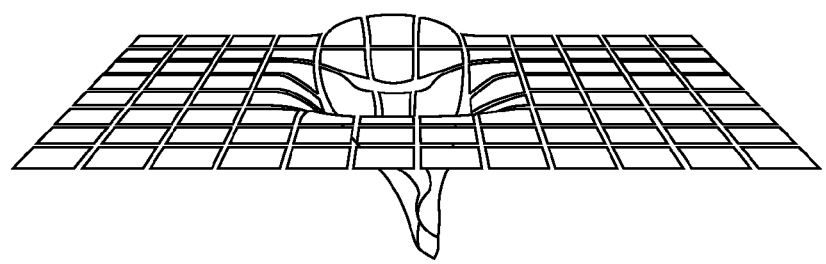
FIG. 2 is a preferred embodiment of a reconstructed visual presentation of the assessed force properties according to the present method.

The force properties thus assessed may be described in numerical values of elements of the force properties. The force properties thus assessed may also be reconstructed to provide a force vector distribution. Upon such reconstruction, certain vectors may be modified for better visualization. FIG. 2 is a preferred embodiment of a reconstructed visual presentation of the assessed force properties according to the present method.

Alternative to the measuring equipment as shown in FIG. 1, the fiber sample and the cover may be provided in a stable position, while only the tactile sensor moves vertically in the upward direction for contacting the fiber end. In this embodiment, a certain length from the end of the fiber sample is outside the cover in the initial position.

The present method may further comprise the step of treating the sample with a composition prior to measurement, which composition is capable of decreasing the stimulus generated by the fiber tip, and/or providing the hair soft. Preferably, the composition is a hair care composition. More preferably, the hair care composition is selected from shampoo, hair conditioning composition, hair styling composition, or combinations thereof. Still more preferably, the composition is a hair conditioning composition.

As used herein, "hair conditioning composition" means a composition comprising at least one conditioning active agent. The conditioning agent for decreasing the stimulus generated by the fiber tip may be selected from conventional conditioning agents, including some silicone components, some fatty alcohol, etc. Suitable examples of hair conditioning agents may be found in the CFTA International Cosmetic Ingredient Dictionary and Handbook, 11$^{th}$ edition, 2006.

The fiber sample is preferably treated with from about 0.01 ml to about 1 ml, more preferably from about 0.05 ml to about 0.5 ml, of composition per gram of fiber sample.

The present method may be useful for demonstrating the benefit of a hair conditioning composition, by comparing the assessed force properties of a fiber sample prior to, and after treatment of the fiber sample with the hair conditioning composition. For such demonstration, an untreated fiber sample and treated fiber sample is compared. Thus, the present invention is also related to a method for demonstrating the benefit of a hair conditioning composition, which composition is capable of decreasing the stimulus generated by the hair fiber tip, or providing the hair soft, said method comprising the steps of:
  (1) providing a sample of one or more fibers to make a first fiber sample and another sample of one or more fibers to make a second fiber sample;
  (2) treating the first fiber sample with a first hair conditioning composition;
  (3) independently assessing the force properties of the fiber tip of the first and second fiber samples according to the method of Claim 1; and
  (4) comparing the assessed force properties of the first and second fiber samples.

The present method may also be useful for demonstrating the benefit of a first hair conditioning composition compared to a second hair conditioning composition, by comparing the assessed force properties of a fiber sample treated with the first hair conditioning composition, and another fiber sample treated with the second hair conditioning composition.

The present invention further relates to a method for marketing a hair conditioning composition by demonstrating the benefit of a hair conditioning composition, which composition is capable of decreasing the stimulus generated by the hair fiber tip, or providing the hair soft, comprising the steps of:
(1) offering for sale the hair conditioning composition,
(2) advertising the benefit of the hair conditioning composition as decreasing the stimulus generated by the hair fiber tip, or providing the hair soft;
(3) demonstrating the decreasing of stimulus generated by the hair fiber tip by conducting the method aforementioned.

EXAMPLE

The following example further describes and demonstrates the preferred embodiments within the scope of the present invention. This example is given solely for the purpose of illustration, and it is not to be construed as limitations of the present invention since many variations thereof are possible without departing from its scope.

Example 1

A fiber sample of human hair switch having a free portion length of 20.32 cm and weight of 4 g is treated with a hair conditioner product commercially available in the Japanese market. Using the measuring equipment as depicted in FIG. 1, the hair switch is clamped onto a means for vertically moving the hair switch, and measured with the following conditions:
the cover is a transparent plastic tube having 20 mm diameter of bore and 195 mm in length;
the distance between the lower end of the cover and tactile sensor is 1.5 mm;
the end of the hair switch is matched with the lower end of the cover;
the fiber sample is moved downward to contact the tactile sensor at speed of 150 cm/min for 3 cm; and
the tactile sensor used is GelForce Version 1.0 available from Nitta Corporation (Osaka, Japan) at recording with gain 300 and threshold 0.005, and played at gain 0.7 and threshold 0.5.

FIG. 2 was obtained as a reconstructed visual presentation of the assessed force properties.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for assessment of force properties generated by the fiber tip of one or more fibers, comprising the steps of:
(a) providing a fiber sample of one or more fibers, the fiber sample having a free portion and an end;
(b) suspending the fiber sample over a tactile sensor at least 0.1 mm away in the vertical direction from the tactile sensor; wherein the fiber sample or the tactile sensor is connected to a means for vertically moving either the fiber sample or the tactile sensor toward each other;
(c) surrounding the free portion of the fiber sample with a cover which surrounds the free portion over some length of the free portion and stably positioned; wherein the cover guides the direction of the free portion in a more or less vertical orientation through the steps hereof;
(d) vertically moving the fiber sample or the tactile sensor such that the end of the fiber sample contacts the tactile sensor;
(e) providing the tactile sensor with means for measuring the distribution of force vectors generated by the contact of the end of the fiber sample; and
(f) assessing the force properties based on the distribution of force vectors, wherein the fiber sample is a strand of mammalian hair having a weight of from about 0.1 g to about 200 g, and a length of from about 1 cm to about 50 cm.

2. The method according to claim 1 wherein the cover is cylindrical.

3. The method according to claim 1 wherein the fiber end and the lower end of the cover is initially in substantially the same horizontal plane, wherein the fiber sample is vertically moved downward for contacting the tactile sensor.

4. The method according to claim 3 wherein the cover is stably positioned at from about 0.1 mm to about 15 mm away in the vertical direction from the tactile sensor.

5. The method according to claim 1 wherein the tactile sensor is vertically moved upward for contacting the fiber end.

6. The method of claim 3 wherein the tactile sensor comprises a transparent elastic body, a set of markers distributed inside the elastic body, and a color CCD camera for acquiring the movements of the markers, wherein the movement is generated by the end of the fiber sample contacting the surface of the elastic body, whereby the elastic body is deformed by the contact and thereby providing variation information of the markers.

7. The method according to claim 6 wherein the fiber sample is continuously vertically moved against the elastic body after contacting the surface of the elastic body.

8. The method according to claim 6 wherein the elastic body has a horizontal plane in the x-y direction and a depth in the z direction, wherein the set of markers are distributed along the x-y direction.

9. The method according to claim 7 wherein the tactile sensor comprises 2 layers of set of markers in 2 different depths in the z direction.

10. The method according to claim 9 wherein the 2 set of markers are provided in different colors.

11. The method according to claim 8 wherein the CCD camera is positioned away from the elastic body in the z direction.

12. The method according to claim 6 wherein the force properties for assessment comprises distribution, magnitude, and direction of the force.

13. The method according to claim 12 wherein the variation information of the markers are reconstructed to provide a force vector distribution.

14. The method according to claim 1 further comprising the step of treating the fiber with a composition prior to measurement, which composition is capable of decreasing the stimulus generated by the hair fiber tip.

15. The method according to claim 14 wherein the composition is a hair conditioning composition.

* * * * *